United States Patent [19]
Moy et al.

[11] Patent Number: 6,025,410
[45] Date of Patent: Feb. 15, 2000

[54] LIQUID OLIGOMERS CONTAINING ACRYLATE UNSATURATION

[75] Inventors: Thomas M. Moy, Hilliard; Laurence Dammann, Powell; Roman Loza, Dublin, all of Ohio

[73] Assignee: Ashland Inc., Dublin, Ohio

[21] Appl. No.: 08/933,784

[22] Filed: Sep. 19, 1997

[51] Int. Cl.$^7$ .......................... C07C 69/72; C07C 69/587; C08F 2/50

[52] U.S. Cl. .......................... 522/182; 522/183; 522/181; 528/306; 560/178; 560/183; 560/205

[58] Field of Search ..................... 522/182, 183, 522/178, 181; 528/306; 560/205, 183, 178

[56] References Cited

U.S. PATENT DOCUMENTS

| | | | |
|---|---|---|---|
| 4,408,018 | 10/1983 | Bartman et al. | 525/300 |
| 4,644,036 | 2/1987 | Walz et al. | 525/386 |
| 5,017,649 | 5/1991 | Clemens | 525/59 |
| 5,416,136 | 5/1995 | Konzmann et al. | 523/414 |
| 5,459,178 | 10/1995 | Chan et al. | |
| 5,496,896 | 3/1996 | Alfons | 525/74 |
| 5,539,017 | 7/1996 | Rheinberger et al. | |

FOREIGN PATENT DOCUMENTS 05880328  8/1993  European Pat. Off. .

OTHER PUBLICATIONS

A Comparison of Catalysts for Crosslinking Acetoacetylated Resins via the Michael Reaction, by Robert J. Clemens and F. Del Rector of Eastman Chemical Products, Inc., Mar. 1989, vol. 61, No. 770.

Michael addition polymers from 1,4 and 1,3 benzene-dimethanol diacetoacetates and tripropylene glycol diacrylate, by David L. Trumbo, The Glidden Company, 16651 Sprague Road, Strongsville, Ohio 44136, USA, *Polymer Bulletin* No. 26, 265–270 (1991).

Michael addition polymers from bisacetoacetates, by David L. Trumbo, The Glidden Company, Strongsville, Ohio 44136, USA, *Polymer Bulletin* 26, 481–485 (1991).

Reaction behavior of monomeric β–ketoesters, by Norbert Moszner, Volker Rheinberger, Ivoclar AG, Benderestrasse , FL–9494 Schaan, Liechtenstein (Received: Oct. 26, 1994) *Macromol, Rapid Commun.* 16, 135–138 (1995).

Applications for Acetoacetyl Chemistry in Thermoset Coatings, by F. Del Rector, W. W. Blount and D. R. Leonard, Eastman Chemical Products, Inc., vol. 61, No. 771, Apr. 1989.

New Polymer Chemistry from Kodak, Eastman Kodak Company, Rochester, New York, Kodak publication JJ–86, *New Polymer Chemistry from Koda*, Mar. 1988.

*Primary Examiner*—Susan W. Berman
*Attorney, Agent, or Firm*—Mary E. Picken

[57] ABSTRACT

The liquid oligomeric compositions of this invention are made by the Michael addition reaction of acetoacetate functional donor compounds with multifunctional acrylate receptor compounds where the equivalent ratios of multifunctional acrylate to acetoacetate vary from $\geq 1:1$ to $\geq 13.2:1$ depending on the functionality of both multifunctional acrylate and acetoacetate. Unuseable gelled or solid oligomer products occur below the claimed ranges. The liquid oligomers of this invention are further crosslinked to make coatings, laminates and adhesives.

9 Claims, No Drawings

LIQUID OLIGOMERS CONTAINING ACRYLATE UNSATURATION

FIELD OF THE INVENTION

This invention relates to liquid oligomers containing unsaturation which can be crosslinked using ultraviolet light without adding costly photoinitators. Films made from the crosslinked oligomers of the inventions are used as protective or decorative coatings on various substrates. The oligomers can be added to other resins used in adhesives or composites.

BACKGROUND OF THE INVENTION

Acrylate, methacrylate and other unsaturated monomers are widely used in coatings, adhesives, sealants, and elastomers, and may be crosslinked by ultraviolet light radiation or peroxide initiated free radical cure. These are typically low molecular weight multifunctional compounds which may be volatile or readily absorbed through skin and can cause adverse health effects. Functionalized polymers may overcome some of these drawbacks; generally, polymers are nonvolatile compounds, not readily absorbed through skin. However, multistep syntheses may be required, low functionality may be detrimental to reactivity and final properties, and catalyst or initiator may be required to effect crosslinking.

The Michael addition of acetoacetate donor compounds to multiacrylate receptor compounds to make crosslinked polymers has been described in the literature. For example, Mozner and Rheinberger reported the Michael addition of acetoacetates having a β-dicarbonyl group to triacrylates and tetracrylates. Macromolecular Rapid Communications 16 135–138 (1995). The products formed were crosslinked gels. In one of the reactions, Mozner added one mole of trimethylol propane triacrylate (TMPTA) having 3 functional groups to one mole of polyethylene glycol (600 molecular weight) diacetoacetate (PEG600-DAA) having two functional groups. (Each "acetoacetate functional group" reacts twice, thus each mole of diacetoacetate has four reactive equivalents.)

Mole Ratio of TMPTA: PEG 600 DAA=1:1

Ratio of acrylate: acetoacetate functional groups=3:2

Ratio of reactive equivalents=3:4

BROAD DESCRIPTION OF THE INVENTION

This invention is the discovery that certain soluble liquid uncrosslinked oligomers, made by one step Michael addition of acetoacetates to multi-acrylates, can be further crosslinked using ultraviolet light without using costly photoinitiators.

We have discovered that when precise proportions of multiacrylate acceptor compounds to acetoacetate donor compounds are combined using a basic catalyst, liquid oligomeric compositions are the product. If proportions below the claimed ranges are used, crosslinked gels or solid products are made which are not useful for the purposes of this invention because only un-gelled, uncrosslinked liquid oligomers will further crosslink without adding photoinitiators. In addition, the liquid oligomer compositions of this invention, since they are liquids, can readily be applied to various substrates using conventional coating techniques such as roll or spray prior to ultraviolet light cure.

The graph illustrates that ratios below the three curves were unuseable gelled materials outside the scope of the invention. Ratios on or above the curves are the liquid oligomers of this invention.

DETAILED DESCRIPTION OF THE INVENTION

Among the multiacrylates used to make the oligomers of this invention are diacrylates, triacrylates, and tetraacrylates.

Useful diacrylates are:

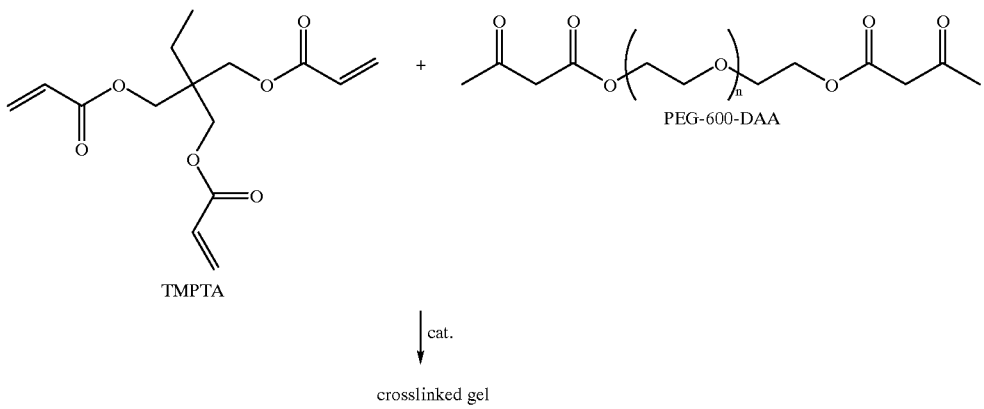

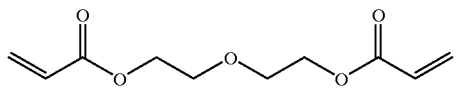
Diethylene Glycol Diacrylate, MW = 214, f = 2

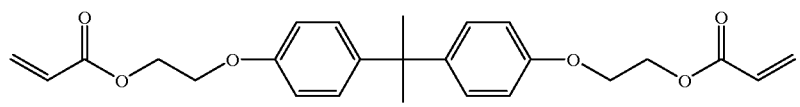
Ethoxylated Bisphenol A Diacrylate, MW = 424, f = 2

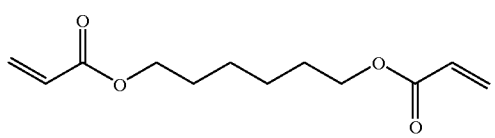
1,6-Hexanediol Diacrylate, MW = 226, f = 2

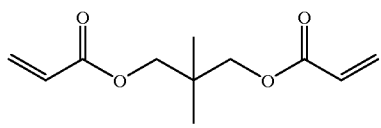
Neopentyl Glycol Diacrylate, MW = 212, f = 2

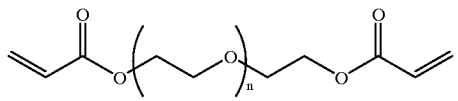
Polyethylene Glycol Diacrylate, MW = 302, 508, f = 2

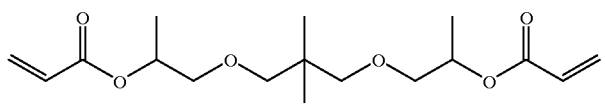
Propoxylated Neopentyl Glycol Diacrylate, MW = 328, f = 2

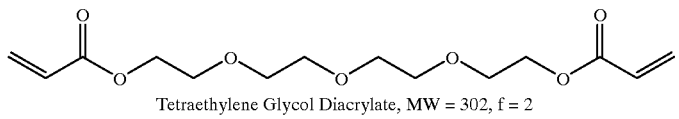
Tetraethylene Glycol Diacrylate, MW = 302, f = 2

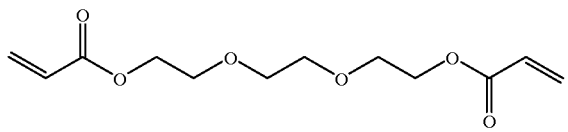
Triethylene Glycol Diacrylate, MW = 258, f = 2

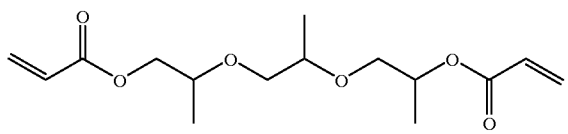
Tripropylene Glycol Diacrylate (TRPGDA), MW = 300, f = 2

Useful triacrylates are:

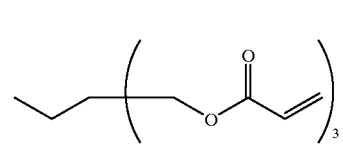
Trimethylolpropane Triacrylate (TMPTA), MW = 296, f = 3

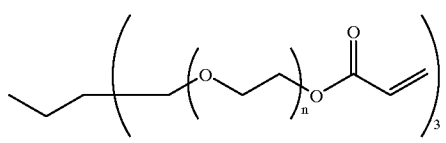
Ethoxylated Trimethylolpropane Triacrylate, MW ≥ 428, f = 3

-continued
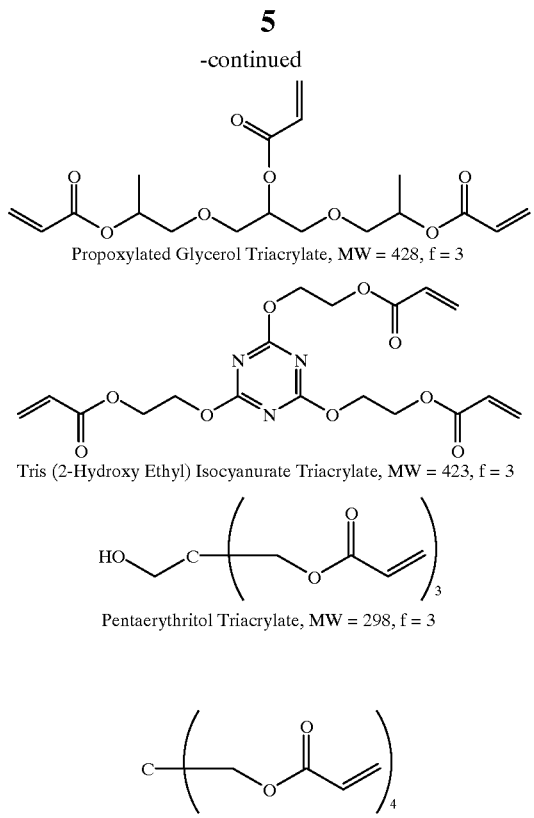
Useful acetoacetates having a reactive equivalent functionality of two are:
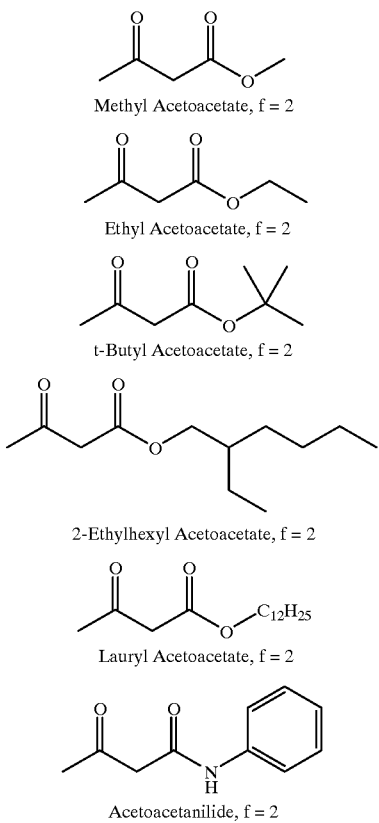
-continued
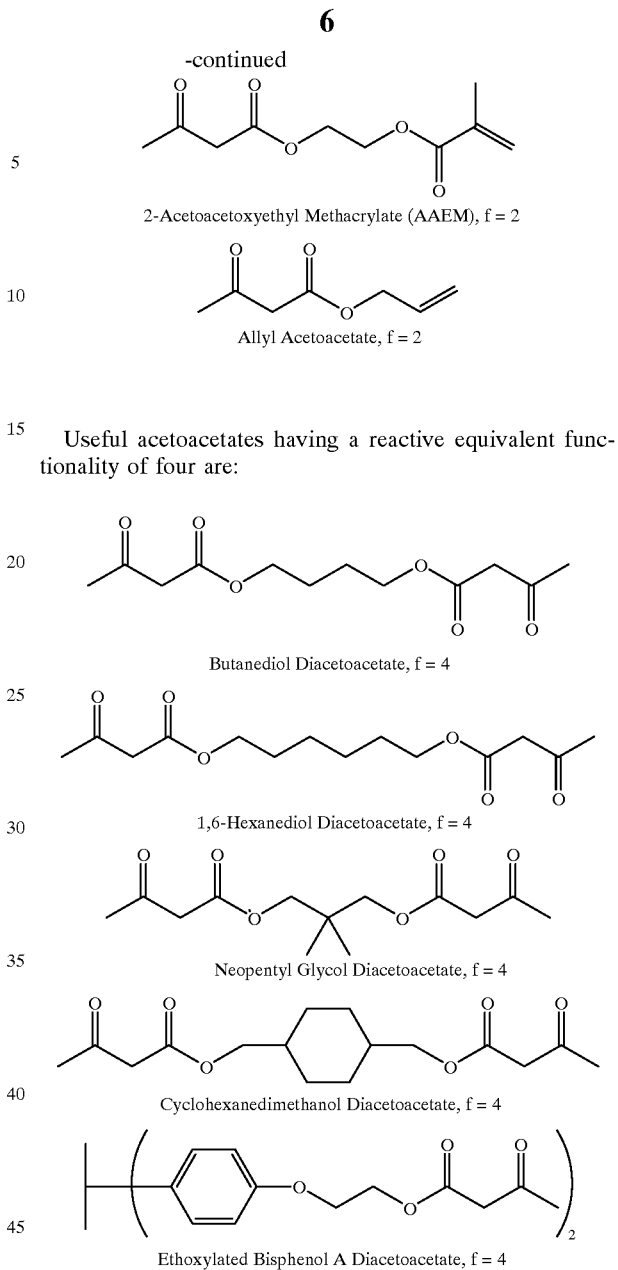
Useful acetoacetates having a reactive equivalent functionality of four are:
Useful acetoacetates having a reactive equivalent functionality of six are:
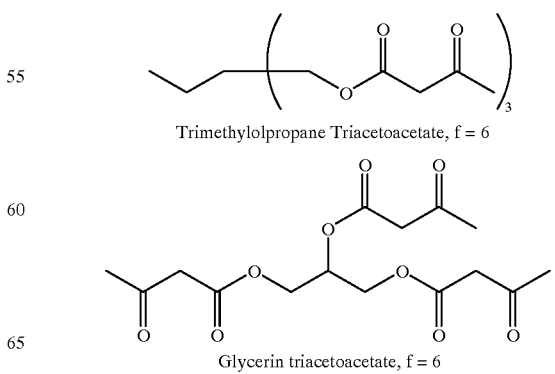

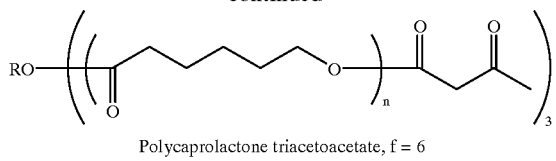

Polycaprolactone triacetoacetate, f = 6

A useful acetoacetate having a reactive equivalent functionality of eight is:

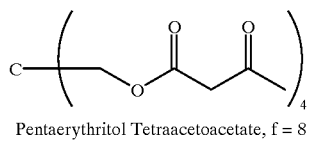

Pentaerythritol Tetraacetoacetate, f = 8

The Michael addition reaction is catalyzed by a strong base; diazabicycloundecene (DBU) is sufficiently strong and readily soluble in the monomer mixtures. Other cyclic amidines, for example diazabicyclo-nonene (DBN) and guanidines are also suitable for catalyzing this polymerization.

Michael addition of a methacrylate functional β-dicarbonyl compound, 2-acetoacetoxyethyl methacrylate (AAEM), to diacrylate monomer yields liquid linear polyesters with reactive pendant methacrylate groups, which can be crosslinked in a subsequent curing reaction. As the acrylate and acetoacetate are mutually reactive and the methacrylate is inert under the conditions of the Michael addition, a highly functionalized (one methacrylate per repeat unit), liquid uncrosslinked polymer can be obtained in a one-step, ambient temperature, solventless reaction. The high selectivity of the Michael reaction permits the use of monomers such as styrene and methyl methacrylate as inert solvents to give low-viscosity systems that are easily incorporated into a variety of laminating resins.

In the following Examples all parts are by weight unless otherwise indicated. In addition, all references mentioned herein are specifically incorporated by reference.

A series of experiments defined the proportions of multi-acrylate to β-dicarbonyl acetoacetate which separate the liquid oligomer products of this invention from the gel or solid products of the prior art.

SYNTHETIC PROCEDURE

An example of resin synthesis is as follows. Trimethylolpropane triacrylate (TMPTA) 59.2 g and diazabicycloundecene (DBU) 0.4 g were weighed into a 500 ml 3-neck round bottom flask equipped with a mechanical stirrer and addition funnel. Ethyl acetoacetate (EAA) 13.0 g was weighed into the addition funnel. The TMPTA and DBU were mixed for 5 minutes prior to addition of the EAA. EAA was then added dropwise to the stirred TMPTA/DBU mixture over a 15 minute period. The solution warmed after addition of EM was complete. After the exotherm subsided a viscous yellow liquid was obtained which did not gel upon standing.

The same general procedure can be employed for a variety of combinations of acrylate and acetoacetate functional reactants, provided the equivalent ratio of acrylate:acetoacetate is sufficient to yield liquid, uncrosslinked products. For particularly exothermic or large scale reactions, controlled, gradual addition of acetoacetate and/or cooling of the reaction may be required to prevent premature, thermally initiated crosslinking of acrylate functional groups.

TABLE 1

Acetoacetate/Acrylate Mixtures

| | aceto-acetate | acrylate | f ratio | mole ratio | equiv ratio | weight ratio | reaction product |
|---|---|---|---|---|---|---|---|
| A | ethyl | hexanediol | 2:2 | 1:1 | 2:2 | 36.5:63.5 | viscous liquid* |
| B | ethyl | penta-erythritol | 2:4 | 1:10 | 1:20 | 3.6:96.4 | viscous liquid* |
| C | butanediol | hexanediol | 4:2 | 1:1 | 2:1 | 53.3:46.7 | cross-linked gel** |
| D | penta-erythritol | penta-erythritol | 8:4 | 1:10 | 1:5 | 11.8:88.2 | cross-linked gel** |

*soluble in methyl ethyl ketone (MEK) at room temperature.
**insoluble in refluxing methyl ethyl ketone.

A and B made useful oligomers of the inventor. C and D made crosslinked gels which are outside the invention.

TABLE 2

Reactions of diacrylate acceptor with acetoacetate-functional donors.

| Acceptor | Donor | Functionality ratio | Mole ratio | Equivalent ratio | Weight ratio | Reaction product |
|---|---|---|---|---|---|---|
| TRPGDA | MeOAcAc | 2:2 | 1:1 | 1:1 | 72.1:27.9 | sol |
| TRPGDA | EtOAcAc | 2:2 | 1:1 | 1:1 | 69.8:30.2 | sol |
| TRPGDA | aceto-acetanilide | 2:2 | 1:1 | 1:1 | 62.9:37.1 | sol |
| TRPGDA | butanediol di-OAcAc | 2:4 | 7.7:1 | 3.9:1 | 90:10 | sol |
| TRPGDA | | 2:4 | 4.9:1 | 2.4:1 | 85:15 | gel |
| TRPGDA | | 2:4 | 3.44:1 | 1.7:1 | 80:20 | gel |
| TRPGDA | cyclohexane dimethanol di- | 2:4 | 19.8:1 | 9.9:1 | 95:05 | sol |
| TRPGDA | di-OAcAc | 2:4 | 13.8:1 | 6.9:1 | 93:7 | sol |
| TRPGDA | | 2:4 | 9.4:1 | 4.7:1 | 90:10 | gel |
| TRPGDA | | 2:4 | 5.9:1 | 2.95:1 | 85:15 | gel |
| TRPGDA | | 2:4 | 4.2:1 | 2.1:1 | 80:20 | gel |
| TRPGDA | neopentyl | 2:4 | 8.2:1 | 4.1:1 | 90:10 | sol |

TABLE 2-continued

Reactions of diacrylate acceptor with acetoacetate-functional donors.

| Acceptor | Donor | Functionality ratio | Mole ratio | Equivalent ratio | Weight ratio | Reaction product |
|---|---|---|---|---|---|---|
| TRPGDA | glycol di-OAcAc | 2:4 | 5.1:1 | 2.6:1 | 85:15 | sol |
| TRPGDA |  | 2:4 | 3.6:1 | 1.8:1 | 80:20 | gel |
| TRPGDA | TONE 0301 tri-OAcAc | 2:6 | 16.6:1 | 5.5:1 | 90:10 | sol |
| TRPGDA |  | 2:6 | 10.4:1 | 3.5:1 | 85:15 | gel |
| TRPGDA |  | 2:6 | 7.4:1 | 2.5:1 | 80:20 | gel |
| TRPGDA | glycerin tri-OAcAc | 2:6 | 10.3:1 | 3.4:1 | 90:10 | sol |
| TRPGDA |  | 2:6 | 6.5:1 | 2.2:1 | 85:15 | gel |
| TRPGDA |  | 2:6 | 4.6:1 | 1.5:1 | 80:20 | gel |
| TRPGDA | penta-erythritol tetra-OAcAc | 2:8 | 14.2:1 | 3.5:1 | 90:10 | sol |
| TRPGDA |  | 2:8 | 8.9:1 | 2.2:1 | 85:15 | gel |
| TRPGDA |  | 2:8 | 6.3:1 | 1.6:1 | 80:20 | gel |

Review of Table 2 shows that certain diacrylate-acetoacetate equivalent ratios make sol or liquid oligomers of the invention.

TABLE 3

Reactions of triacrylate acceptor with acetoacetate-functional donors.

| Acceptor | Donor | Functionality ratio | Mole ratio | Equivalent ratio | Weight ratio | Reaction product |
|---|---|---|---|---|---|---|
| TMPTA | EtOAcAc | 3:2 | 2:1 | 3:1 | 82:18 | sol |
| TMPTA | EtOAcAc | 3:2 | 3:2 | 2.25:1 | 77.4:22.6 | sol |
| TMPTA | EtOAcAc | 3:2 | 4:3 | 2:1 | 75.2:24.8 | gel |
| TMPTA | butanediol di-OAcAc | 3:4 | 7.8:1 | 5.9:1 | 90:10 | sol |
| TMPTA |  | 3:4 | 4.9 1 | 3.7:1 | 85:15 | gel |
| TMPTA |  | 3:4 | 3.5:1 | 2.6:1 | 80:20 | gel |
| TMPTA | cyclohexane dimethanol di-di-OAcAc | 3:4 | 9.5:1 | 7.1:1 | 90:10 | sol |
| TMPTA |  | 3:4 | 6.0:1 | 4.5:1 | 85:15 | gel |
| TMPTA |  | 3:4 | 4.2:1 | 3.2:1 | 80:20 | gel |
| TMPTA | neopentyl glycol di-OAcAc | 3:4 | 8.3:1 | 6.2:1 | 90:10 | sol |
| TMPTA |  | 3:4 | 5.2:1 | 3.9:1 | 85:15 | gel |
| TMPTA |  | 3:4 | 3.7:1 | 2.8:1 | 80:20 | gel |
| TMPTA | TONE 0301 tri-OAcAc | 3:6 | 16.8:1 | 8.4:1 | 90:10 | sol |
| TMPTA |  | 3:6 | 10.6:1 | 5.3:1 | 85:15 | gel |
| TMPTA | glycerin tri-OAcAc | 3:6 | 14.3:1 | 7.2:1 | 92.5:7.5 | sol |
| TMPTA |  | 3:6 | 10.5:1 | 5.2:1 | 90:10 | gel |
| TMPTA | penta-erythritol tetra-OAcAc | 3:8 | 30.3:1 | 11.4:1 | 95:5 | sol |
| TMPTA |  | 3:8 | 19.7:1 | 7.4:1 | 92.5:7.5 | sol |
| TMPTA |  | 3:8 | 14.4:1 | 5.4:1 | 90:10 | gel |

Review of Table 3 shows that certain triacrylate:acetoacetate ratios make sol or liquid oligomers of the invention.

TABLE 4

Reactions of tetracrylate acceptor with acetoacetate-functional donors.

| Acceptor | Donor | Functionality ratio | Mole ratio | Equivalent ratio | Weight ratio | Reaction product |
|---|---|---|---|---|---|---|
| PETA | EtOAcAc | 4:2 | 3.3:1 | 6.6:1 | 90:10 | sol |
| PETA | EtOAcAc | 4:2 | 2:1 | 4.0:1 | 84.4:15.6 | gel |

TABLE 4-continued

Reactions of tetracrylate acceptor with acetoacetate-functional donors.

| Acceptor | Donor | Functionality ratio | Mole ratio | Equivalent ratio | Weight ratio | Reaction product |
|---|---|---|---|---|---|---|
| PETA | EtOAcAc | 4:2 | 1:1 | 2:1 | 73:27 | gel |
| PETA | butanediol di-OAcAc | 4:4 | 13.9:1 | 13.9:1 | 95:5 | sol |
| PETA |  | 4:4 | 9.7 1 | 9.7:1 | 93:7 | sol |
| PETA |  | 4:4 | 6.6:1 | 6.6:1 | 90:10 | gel |
| PETA | cyclohexane dimethanol di-di-OAcAc | 4:4 | 16.8:1 | 16.8:1 | 95:5 | sol |
| PETA | di-OAcAc | 4:4 | 8.0:1 | 8:1 | 90:10 | gel |
| PETA | neopentyl glycol di-OAcAc | 4:4 | 14.7:1 | 14.7:1 | 95:5 | sol |
| PETA |  | 4:4 | 10.3:1 | 10.3:1 | 93:7 | sol |
| PETA |  | 4:4 | 7.0:1 | 7:1 | 90:10 | gel |
| PETA | TONE 0301 tri-OAcAc | 4:6 | 29.8:1 | 19.9:1 | 95:5 | sol |
| PETA |  | 4:6 | 20.8:1 | 13.9:1 | 93:7 | sol |
| PETA |  | 4:6 | 14.1:1 | 9.4:1 | 90:10 | gel |
| PETA | glycerin tri-OAcAc | 4:6 | 18.6:1 | 12.4:1 | 95:5 | sol |
| PETA |  | 4:6 | 12.1:1 | 8:1 | 92.5:7.5 | gel |
| PETA | penta-erythritol tetra-OAcAc | 4:8 | 65.7:1 | 32.9:1 | 98:2 | sol |
| PETA |  | 4:8 | 43.3:1 | 21.7:1 | 97:3 | sol |
| PETA |  | 4:8 | 32.2:1 | 16.1:1 | 96:4 | sol |
| PETA |  | 4:8 | 25.5:1 | 12.7:1 | 95:5 | sol |
| PETA |  | 4.8 | 17.8:1 | 8.9:1 | 93:7 | gel |
| PETA |  | 4:8 | 12.1:1 | 6:1 | 90:10 | gel |

Review of Table 4 shows that certain tetracrylate:acetoacetate ratios make sol or liquid oligomers of the invention.

In order to demonstrate ultraviolet light crosslinking of these liquid oligomers, samples containing 1% (wt) Irgacure 500 photoinitiator and 0% photoinitiator were applied to release liner and spread to a thickness of 1.5 mil. Specimens were cured on a Fusion Systems Corp. uv curing unit, using an H-bulb and belt speed of 20–25 feet/minute; all formed transparent, flexible, nearly colorless films. Samples of each film were weighed, immersed in acetone (a good solvent for the uncured resins) at room temperature for 48 hours, blotted dry and re-weighed to determine solvent uptake. Specimens were then dried to constant weight in a vacuum oven at 80° C. to determine gel fractions; these values are listed in the table 5 below.

TABLE 5

Solvent Uptake and Gel Fractions of UV Cured Methacrylate Functional Polyesters.

| DIACRYLATE | Solvent Uptake, % (Irgacure 500, 1%) | Gel Fraction (Irgacure 500, 1%) | Solvent Uptake, % (No Photo-initiator) | Gel Fraction (No Photo-initiator) |
|---|---|---|---|---|
| NPG | 18 | 94% | 9 | 96% |
| PEG 200 | 19 | 96% | 18 | 94% |
| Hexanediol | 12 | 96% | 9 | 96% |
| Triethylene glycol | 16 | 95% | 19 | 96% |

These results confirm that the products are crosslinked and indicate no significant difference between products cured with or without added photoinitiator. This suggests that the pendant methyl ketone substituents serve as an internal or "built in" photoinitiator. To further demonstrate the role of methyl ketone substituents in the uv cure of these resins, three acrylate terminal resins were prepared from neopentyl glycol diacrylate and various b-dicarbonyl compounds in a 5:4 molar ratio. β-dicarbonyl compounds included acetylacetone (2 methyl ketones per molecule), ethyl acetoacetate (1 ketone/molecule) and diethyl malonate (no ketones). UV cure was performed as before, without added photoinitiator. Resins containing acetylacetone or ethyl acetoacetate cured to soft, tacky films. Such films are useful in protective or decorative coatings on wood, or metal substrates. The resin containing diethyl malonate failed to cure, remaining liquid.

We claim:

1. A method of making a liquid oligomeric composition, stable for more than one month, having residual pendant unsaturated acrylate groups, useful as a coating when further polymerized in the absence of added photoinitiator, comprising the step of reacting an acetoacetate donor having two, four, six, or eight reactive equivalent functional groups per molecule provided by acetoacetate groups and an excess of acrylate acceptor selected from the group of diacrylate, triacrylate, and tetra-acrylate in the presence of a strong base wherein the reactive equivalent functionality ratios are:

a) diacrylate:acetoacetate of
 $\geq$1:1 where acetoacetate functionality=2
 $\geq$4.5:1 where acetoacetate functionality=4
 $\geq$4.5:1 where acetoacetate functionality=6,
 $\geq$3.5:1 where acetoacetate functionality=8, b) triacrylate:acetoacetate of
 $\geq$2.25 where acetoacetate functionality=2
 $\geq$6.4:1 where acetoacetate functionality=4,
 $\geq$7.8:1 where acetoacetate functionality=6,
 $\geq$7.4:1 where acetoacetate functionality=8 c) tetraacrylate:acetoacetate of
 $\geq$6.6 where acetoacetate functionality=2
 $\geq$12.3 :1 where acetoacetate functionality=4

≧13.2.1 where acetoacetate functionality=6
≧12.7:1 where acetoacetate functionality=8,
wherein said diacrylate is selected from the group of
  diethylene glycol diacrylate,
  ethoxylated bisphenol A diacrylate,
  1.6-hexanediol diacrylate,
  neopentyl glycol diacrylate,
  polyethylene glycol (Mn200) diacrylate,
  polyethylene glycol (Mn400) diacrylate,
  propoxylated neopentyl glycol diacrylate,
  tetraethylene glycol diacrylate,
  triethylene glycol diacrylate,
  tripropylene glycol diacrylate, and
wherein said triacrylate is selected from the group of
  trimethylolpropane triacrylate,
  ethoxylated trimethylolpropane triacrylate,
  tris (2-hydroxyethyl) isocyanurate triacrylate,
  propoxylated glycerol triacrylate, and
  pentaerythritol triacrylate, and
wherein said tetraacrylate is pentaerythritol tetraacrylate.

2. The method of claim 1 wherein acetoacetates having 2 reactive equivalent functional groups per molecule provided by acetoacetate groups are
  ethyl acetoacetate,
  t-butylacetoacetate,
  methyl acetoacetate,
  2-ethylhexyl acetoacetate,
  lauryl acetoacetate,
  acetoacetanilide,
  2-acetoacetoxyethyl methacrylate, or
  allyl acetoacetate.

3. The method of claim 1 wherein acetoacetates having 4 reactive equivalent functional groups per molecule provided by acetoacetate groups are
  1,4- butanediol diacetoacetate
  1,6-hexanediol diacetoacetate,
  neopentyl glycol diacetoacetate,
  cyclohexane dimethanol diacetoacetate, or
  ethoxylated bisphenol A diacetoacetate.

4. The method of claim 1 wherein acetoacetates having 6 reactive equivalent functional groups per molecule provided by acetoacetate groups are
  trimethylol propane triacetoacetate,
  glycerin triacetoacetate, and
  polycaprrolactone triacetoacetate.

5. The method of claim 1 said acetoacetate having 8 reactive equivalent functional group per molecule provided by acetoacetate groups is pentaerythritol tetraacetoacetate.

6. The method of claim 1 wherein said strong base is diazabicycloundecene (DBU).

7. The method of claim 1 wherein said reaction between a Michael donor acetoacetate and a Michael acceptor acrylate occurs in the presence of a solvent inert in the Michael reaction.

8. The method of claim 7 wherein said solvent is styrene, t-butyl styrene, α-methyl styrene, vinyl toluene, vinyl acetate, allyl acetate, allyl methacrylate, diallyl phthalate, $C_1$–$C_{18}$ methacrylate esters, dimethacrylates or trimethacrylates.

9. The method of claim 1 further comprising a photoinitiator.

* * * * *